United States Patent
Richter et al.

(10) Patent No.: US 7,208,635 B2
(45) Date of Patent: Apr. 24, 2007

(54) METHOD FOR THE HYDROFORMYLATION OF OLEFINS WITH 2 TO 6 CARBON ATOMS

(75) Inventors: Wolfgang Richter, Wachenheim (DE); Rolf Müller, Dannstadt-Schauernheim (DE); Roland Krokoszinski, Weisenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 232 days.

(21) Appl. No.: 10/500,722

(22) PCT Filed: Jan. 16, 2003

(86) PCT No.: PCT/EP03/00419

§ 371 (c)(1),
(2), (4) Date: Jul. 6, 2004

(87) PCT Pub. No.: WO03/059859

PCT Pub. Date: Jul. 24, 2003

(65) Prior Publication Data

US 2005/0119509 A1     Jun. 2, 2005

(30) Foreign Application Priority Data

Jan. 17, 2002   (DE) ............................. 102-01-676

(51) Int. Cl.
*C07C 45/00*  (2006.01)
*C07C 67/38*  (2006.01)

(52) U.S. Cl. .................. 568/454; 568/451; 560/233

(58) Field of Classification Search ................ 568/454, 568/451; 560/233
See application file for complete search history.

(56) References Cited

U.S. PATENT DOCUMENTS

| | | | | |
|---|---|---|---|---|
| 4,523,036 | A | | 6/1985 | Cornils et al. |
| 4,525,036 | A | * | 6/1985 | Fujibayashi et al. ........ 359/688 |
| 4,577,043 | A | * | 3/1986 | Kalbfell et al. ............. 568/454 |
| 4,778,929 | A | * | 10/1988 | Zehner et al. ............... 568/454 |
| 6,049,011 | A | * | 4/2000 | Kiss et al. ................... 568/451 |
| 6,100,432 | A | * | 8/2000 | Borgel et al. ............... 568/454 |
| 6,642,420 | B1 | | 11/2003 | Zehner et al. |
| 2003/0153791 | A1 | | 8/2003 | Richter et al. |
| 2003/0176743 | A1 | | 9/2003 | Walz et al. |
| 2004/0015011 | A1 | | 1/2004 | Krokoszinski et al. |
| 2004/0024259 | A1 | | 2/2004 | Richter et al. |

FOREIGN PATENT DOCUMENTS

WO     97/20793     6/1997

OTHER PUBLICATIONS

Ullmann's Encyclopedia of Industrial Chemistry, 5$^{th}$ Ed., vol. B4 (XP992238440) 1992.

* cited by examiner

*Primary Examiner*—Samuel A Barts
*Assistant Examiner*—Lalitha Nagubandi
(74) *Attorney, Agent, or Firm*—Novak Druce & Quigg LLP

(57) ABSTRACT

The invention relates to a hydroformylation process in which at least one olefin having from 2 to 6 carbon atoms is reacted continuously with carbon monoxide and hydrogen in the presence of a hydroformylation catalyst in a reaction zone in which a liquid phase is present and a stream S) is taken from the liquid phase, heat is removed from this stream and the stream is subsequently returned to the reaction zone without removal of a material component.

9 Claims, No Drawings

METHOD FOR THE HYDROFORMYLATION OF OLEFINS WITH 2 TO 6 CARBON ATOMS

The present invention relates to a hydroformylation process in which at least one olefin having from 2 to 6 carbon atoms is reacted continuously with carbon monoxide and hydrogen in the presence of a hydroformylation catalyst in a reaction zone.

Hydroformylation or the oxo process is an important industrial process for preparing aldehydes from olefins, carbon monoxide and hydrogen. These aldehydes can, if desired, be hydrogenated by means of hydrogen in the same process or subsequently in a separate hydrogenation step to produce the corresponding alcohols. Hydroformylation is carried out in the presence of catalysts which are homogeneously dissolved in the reaction medium. Catalysts used are generally compounds or complexes of metals of transition group VIII, especially Co, Rh, Ir, Pd, Pt or Ru compounds or complexes which may be unmodified or, for example, modified with amine- or phosphine-containing compounds.

Hydroformylation is an exothermic reaction which, particularly when using short-chain olefins, liberates a considerable quantity of heat which has to be removed from the reactor used for the reaction. It is known that cooling of the contents of the reactor can be achieved using heat exchangers e.g. in the form of cooling coils which are, for example, welded onto the outside of the reactor wall or pass through the interior of the reactor and through which an auxiliary medium for heat transfer (cooling medium) usually flows. These auxiliary media are, for example, water or other liquids which have a high thermal conductivity and heat capacity. However, heat exchangers connected to the hydroformylation reactor have a number of disadvantages. Thus, reactors having cooling coils welded onto the reactor wall are restricted in size since as the reactor size increases, the surface available for cooling becomes too small relative to the reactor volume. Reactors having internal heat exchangers, e.g. cooling matrices, are complicated in terms of their construction and expensive. In addition, in the case of reactors having external and/or internal heat exchangers, it is frequently necessary to mix the contents of the reactor by means of suitable measures, e.g. the use of stirrers, to ensure effective removal of the heat of reaction.

The German patent applications DE-A-100 31 517, 100 31 518, 100 31 519 and 100 31 520 describe processes for the hydroformylation of olefins.

U.S. Pat. No. 4,577,043 describes a hydroformylation process for preparing aldehydes in the presence of water and a water-soluble catalyst, in which a product-containing stream is discharged from the reactor; this is firstly separated into a liquid phase and a gaseous phase and the liquid phase is further separated into an aqueous phase and an organic phase, with the individual separation steps being carried out without prior cooling of the stream. Only after the separation is the organic phase cooled, for which purpose it is possible to use a heat exchanger which serves to preheat the synthesis gas and/or olefin used in the reaction.

U.S. Pat. No. 4,523,036 describes a continuous process for preparing aldehydes from olefins and synthesis gas, in which a phase separation without prior cooling is carried out to isolate the reaction products. This phase separation can, according to a first embodiment, be carried out in a phase separation vessel which is physically separate from the hydroformylation reactor. The heat generated by the process can subsequently be utilized in a downstream heat exchanger. According to a second embodiment, phase separation is carried out in special constructions at the top of the reactor. Here, the heat generated by the process can be removed by means of a cooling matrix. In both cases, the heat of reaction can be removed without use of an auxiliary medium for heat transfer and be used for preheating the starting materials or in the distillation of the products.

Coupling the removal of the heat of reaction with the isolation of desired products as described in the abovementioned documents is likewise associated with disadvantages. Any necessary thermal insulation of apparatuses downstream of the hydroformylation reactor, e.g. phase separation vessels, is complicated and expensive. In addition, coupling of heat and mass transport can be matched only to a limited extent to the reaction conditions when, for example, the quantity of heat which has to be removed is greater than that compatible with the isolation of products.

It is an object of the present invention to provide a hydroformylation process in which the heat of reaction can be removed effectively and simply and can wherever possible be used again in a beneficial way.

We have found that this object is achieved by a hydroformylation process in which at least one olefin having from 2 to 6 carbon atoms is reacted continuously with carbon monoxide and hydrogen in the presence of a hydroformylation catalyst in a reaction zone in which a liquid phase is present and a stream S) is taken from the liquid phase, heat is removed from this stream and the stream is subsequently returned to the reaction zone without removal of a material component.

In the process of the present invention, the reaction is preferably carried out in a reaction apparatus containing a liquid phase and a gas phase. The liquid phase is preferably essentially homogeneous and comprises the hydroformylation catalyst together with the dissolved reactants. To remove the heat of reaction, a stream S) is taken from the liquid phase, heat is withdrawn from this stream by cooling and it is subsequently returned to the reaction zone. According to the process of the present invention, no material component, e.g. products, starting materials, etc., is separated off from the stream taken from the reaction zone for the removal of heat.

The heat is preferably withdrawn from the stream by bringing it into contact with a heat exchanger. Suitable heat exchangers are the customary apparatuses for heat transfer in which heat is transported from one place or medium to another. They can have customary constructions, e.g. plate, annular groove, ribbed tube, lamellar, shell-sand-tube, split tube, plate, spiral, block, scraper, screw, helical, fluidized-bed, candle, cooled circulation and two- and three-coil exchangers and recuperators. The withdrawal of the heat can be achieved, for example, by bringing the stream S) into contact with a cooling medium. For this purpose, the heat exchangers can be configured, for example, as water coolers or air coolers. However, in a preferred embodiment, the heat withdrawn from the stream S) is used in a heat-consuming step of the hydroformylation process or another process. In this case, it is advantageous for the stream S) taken from the hydroformylation reaction to be conveyed to the place where heat is consumed without the heat present in it being transferred to an auxiliary medium in between. This can be carried out, for example, via customary pipes which may be thermally insulated and pressure-rated if necessary. Suitable heat-consuming steps in the hydroformylation process which are suitable for use of the recovered process heat are described in more detail below. They include, in particular:

preheating of the reactants (synthesis gas and/or starting olefin), thermal separation and purification steps in the work-up of the output from the reaction.

In general, the stream returned to the reaction zone has a temperature which is from about 5 to 15° C. below the temperature in the reaction zone.

Olefins which can be hydroformylated in the process of the present invention contain from 2 to 6 carbon atoms. They can be straight-chain, branched or cyclic olefins. Preferred examples of suitable olefins are ethene, propene, 1-butene and 2-butene. The olefin is generally fed in the form of an olefin-containing feed stream into the reaction zone. In a useful embodiment of the process of the present invention, the olefin-containing feed stream and/or the synthesis gas can be heated by means of the heat removed from the reaction zone prior to being fed into the reaction zone. The olefin-containing feed stream can comprise a single olefin or a mixture of olefins. The process of the present invention is particularly useful for the use of propylene to produce n-butanal and isobutanal. However, the use of ethylene to produce propionaldehyde or of 1-butene to produce n-valeraldehyde and isovaleraldehyde can also be advantageous. The olefin-containing feed stream used can further comprise a proportion of a saturated hydrocarbon, generally a saturated hydrocarbon having the same number of carbon atoms as the olefin used. To prevent a continuous rise in the concentration of the saturated hydrocarbon in the reaction zone, it is then generally necessary to provide for (at least part of) the saturated hydrocarbon to be separated off at one point in the process.

Carbon monoxide and hydrogen are usually used in the form of a mixture, namely synthesis gas. The composition of the synthesis gas used in the process of the present invention can vary within a wide range. The molar ratio of carbon monoxide to hydrogen is generally from 2:1 to 1:2, in particular from about 45:55 to 50:50.

The temperature in the hydroformylation reaction is generally in a range from about 50 to 200° C., preferably from about 60 to 190° C., in particular from about 90 to 190° C. The reaction is preferably carried out at a pressure in the range from about 10 to 700 bar, more preferably from 15 to 200 bar, in particular from 15 to 60 bar. The reaction pressure can be varied as a function of the activity of the hydroformylation catalyst used.

Suitable pressure-rated reaction apparatuses for hydroformylation are known to those skilled in the art. They include the generally customary reactors for gas/liquid reactions, e.g. gas circulation reactors, bubble columns, etc., which may be subdivided by means of internals. The process of the present invention advantageously makes it possible to use simpler and cheaper reactors in which the use of complicated cooling facilities, e.g. cooling coils installed on the outer surface or in the interior or cooling matrices, can be dispensed with. Preference is given to bubble column reactors. It is advantageous that the reactor size in the process of the present invention is not limited to any significant extent by the necessity of cooling the reaction mixture, as is the case in processes known from the prior art.

Suitable hydroformylation catalysts are the customary transition metal compounds and complexes known to those skilled in the art, which can be used either with or without cocatalysts. The transition metal is preferably a metal of transition group VIII of the Periodic Table, in particular Co, Ru, Rh, Pd, Pt, Os or Ir, especially Rh, Co, Ir or Ru.

Suitable complexes are, for example, the carbonyl compounds of the abovementioned metals and also complexes whose ligands are selected from among amines, arylphosphines, alkylphosphines, arylalkylphosphines, olefins, dienes, etc., and mixtures thereof.

Examples of suitable complexes are rhodium complexes of the formula $RhX_mL^1L^2(L^3)_n$, where X is halide, preferably chloride or bromide, alkylcarboxylate or arylcarboxylate, acetylacetonate, arylsulfonate or alkylsulfonate, in particular phenylsulfonate and toluenesulfonate, hydride or the diphenyltriazine anion, $L^1$, $L^2$, $L^3$ are each, independently of one another, CO, an olefin, a cycloolefin, preferably cyclooctadiene (COD), dibenzophosphole, benzonitrile, $PR_3$ or $R_2P$-A-$PR_2$, m is 1 or 3 and n is 0, 1 or 2. The radicals R can be identical or different and are alkyl, cycloalkyl and aryl radicals, preferably phenyl, p-tolyl, m-tolyl, p-ethylphenyl, p-cumyl, p-t-butylphenyl, p-$C_1$–$C_4$-alkoxyphenyl, preferably p-anisyl, xylyl, mesityl, p-hydroxyphenyl which may also be in ethoxylated form, sulfophenyl, isopropyl, $C_1$–$C_4$-alkoxy, cyclopentyl or cyclohexyl. A is 1,2-ethylene or 1,3-propylene. $L^1$, $L^2$ and $L^3$ are preferably each, independently of one another, CO, COD, P(phenyl)$_3$, P(i-propyl)$_3$, P(anisyl)$_3$, P(OC$_2$H$_5$)$_3$, P(cyclohexyl)$_3$, dibenzophosphole or benzonitrile.

X is preferably hydride, chloride, bromide, acetate, tosylate, acetylacetonate or the diphenyltriazine anion, in particular hydride, chloride or acetate.

Preferred hydroformylation catalysts are phosphorus-containing rhodium catalysts as are, for example, formed in-situ under hydroformylation conditions from a rhodium source and a triarylphosphine such as triphenylphosphine, for example $RhH(CO)_2(PPh_3)_2$ or $RhH(CO)(PPh_3)_3$.

Suitable hydroformylation catalysts are described for example, in Beller et al., Journal of Molecular Catalysis A, 104 (1995), p. 17–85, which is hereby fully incorporated by reference.

A preferred embodiment is a continuous process in which i) an olefin-containing feed stream comprising at least one olefin having from 2 to 6 carbon atoms and also carbon monoxide and hydrogen are fed into a reaction zone and reacted in the presence of a hydroformylation catalyst, where a liquid phase is present in the reaction zone and a stream S) is taken from this liquid phase, heat is withdrawn from the stream and the stream is subsequently returned to the reaction zone without removal of a material component, ii) an output is taken from the reaction zone and is subjected to a single-stage or multistage separation operation to give at least one stream comprising the major part of the hydroformylation product and a stream comprising the major part of the unreacted olefin, and iii) at least part of the stream comprising the major part of the unreacted olefin is returned to the reaction zone.

In general, partial conversion, based on the olefin fed in, takes place per pass in the reaction zone. The conversion is generally from 10 to 90% based on the olefin fed in.

The output from the reaction zone can be subjected to a single-stage or multistage separation operation to give at least one stream comprising the major part of the hydroformylation product and a stream comprising the major part of the unreacted olefin. The saturated hydrocarbons which may be present in the olefin used and the saturated hydrocarbons which may be formed as by-products of the hydroformylation are generally also present in the stream comprising the major part of the olefin. Depending on the method of discharge, further streams such as offgases comprising synthesis gas and streams comprising high-boiling by-products of the hydroformylation and/or hydroformylation catalyst may be obtained and these are, if appropriate after work-up, returned wholly or in part to the reaction zone or discharged from the process. It is possible, for example, firstly to separate off the hydroformylation product and any components having boiling points higher than that of the hydroformylation product from the output from the reaction zone. Unreacted olefin, possibly in admixture with saturated hydrocarbon, can subsequently be condensed out. The heat consumed in the individual separation steps can be at least partly covered by the heat withdrawn from the reaction zone.

In a useful embodiment, the stream consisting essentially of unreacted olefin and possibly saturated hydrocarbon is, however, obtained by firstly separating off a crude hydroformylation product which contains unreacted olefin and possibly saturated hydrocarbon in dissolved form from the output from the reaction zone and then subjecting the liquid crude hydroformylation product to a degassing step in which a stream consisting essentially of unreacted olefin and possibly saturated hydrocarbon is obtained. The reaction output which has been freed of the crude hydroformylation product is generally returned wholly or in part to the reaction zone. To achieve degassing, the crude hydroformylation product can be depressurized, heated and/or treated with a stripping gas such as synthesis gas or nitrogen. Degassing is advantageously carried out in a column by, for example, feeding the crude hydroformylation product into the middle region of the column, taking off the degassed hydroformylation product at the bottom of the column and passing it to further work-up and taking off a liquid or gaseous stream consisting essentially of unreacted olefin and saturated hydrocarbon at the top of the column. The heat consumption of the degassing column is preferably at least partly covered by the heat withdrawn from the reaction zone.

The separation of the crude hydroformylation product from the output from the reaction zone can be carried out in various ways. It is possible, for example, to use the liquid discharge process in which the essentially liquid, except for the synthesis gas used in excess for the hydroformylation, output from the reaction zone is depressurized so as to separate it into a liquid phase consisting essentially of high-boiling by-products, the homogeneously dissolved hydroformylation catalyst, possibly part of the hydroformylation product and small amounts of unreacted olefin and of saturated hydrocarbon and a gas phase consisting essentially of hydroformylation product, unreacted olefin and saturated hydrocarbon together with unreacted synthesis gas. The liquid phase can be returned as recycle stream to the reactor. The crude hydroformylation product is obtained by at least partial condensation of the gas phase. The gas phase remaining after the condensation is wholly or partly returned to the reaction zone.

The gaseous and liquid phases obtained initially in the depressurization stage can advantageously be worked up by the process described in WO 97/07086. For this purpose, the liquid phase is heated and introduced into the upper region of a column, while the gas phase is fed in at the bottom of the column. The liquid phase can be heated at least partly by means of the heat withdrawn from the reaction zone. Liquid phase and gas phase are conveyed through the column in countercurrent. To increase the mutual contact of the phases, the column is preferably packed with packing elements. The intimate contact of the gas phase with the liquid phase results in the residual hydroformylation product, unreacted olefin and saturated hydrocarbon present in the liquid phase being transferred to the gas phase, so that the gas stream leaving the top of the column is enriched in hydroformylation product, unreacted olefin and saturated hydrocarbon compared to the gas stream introduced at the lower end of the column. The further work-up of the gas stream leaving the column and of the liquid phase leaving the column is carried out in a customary manner, for example as described above.

As an alternative, it is possible to employ, particularly when using $C_2$–$C_4$-olefins, the gas recycle process in which a gas stream is taken off from the gas space of the hydroformylation reactor. This gas stream consists essentially of synthesis gas, unreacted olefin and possibly saturated hydrocarbon together with amounts, depending on the vapor pressure in the hydroformylation reactor, of the hydroformylation product formed in the hydroformylation reaction. The entrained hydroformylation product is condensed from the gas stream, for example by cooling, and the gas stream which has been freed of the liquid component is recirculated to the hydroformylation reactor.

The stream consisting essentially of unreacted olefin and possibly saturated hydrocarbon comprises, for example, from 50 to 100% by weight, preferably from 50 to 95% by weight, of olefin and may contain from 5 to 50% by weight of saturated hydrocarbons.

If the stream comprising the major part of the unreacted olefin still contains saturated hydrocarbons, it can be separated into an olefin-enriched fraction and an olefin-depleted fraction by customary separation methods, e.g. distillation or membrane filtration. Distillation (rectification) is usually carried out at low temperature and/or superatmospheric pressure, with the precise temperature and/or pressure conditions depending on factors such as the number of carbon atoms in the olefin/saturated hydrocarbon to be separated, etc. Rectification is generally carried out in a column which is provided with a sufficiently large number of rectification trays. Columns for such separation tasks are known per se and are used, for example, for the separation of olefins and saturated hydrocarbons present in the output gas from a steam cracker. The stream to be fractionated can be introduced in either gaseous or liquid form into the column, preferably in the middle region of the column. The olefin-enriched fraction can advantageously be taken off at the top or in the upper region of the column, while the olefin-depleted fraction can be taken off at the bottom or in the lower region of the column. The heat requirement of the separation into an olefin-enriched fraction and an olefin-depleted fraction can be covered at least partly by the heat withdrawn from the reaction zone.

In general, efforts are made to obtain a very pure saturated hydrocarbon as olefin-enriched fraction so that it can be discharged from the process without any great loss of olefin. On the other hand, it is generally not necessary or even desirable for the olefin-enriched fraction to be pure olefin, but instead a certain amount of saturated hydrocarbons is left therein so as to reduce the outlay for the separation.

In a preferred embodiment of the process of the present invention, a propylene-containing feed stream is used. If this further comprises propane or propane is formed as by-product in the hydroformylation, a mixture of propylene and propane is obtained as stream to be fractionated. The separation of this stream into a propylene-enriched fraction and a propylene-depleted fraction is carried out under pressure in a suitable distillation column, namely a $C_3$ splitter. The column is preferably operated so that a propylene-enriched fraction which can be returned directly to the reaction zone is obtained at the top and substantially pure propane which can be removed from the system without loss of propylene can be taken off at the bottom. Typical operating conditions for the $C_3$ splitter are: pressure at the top from 20 to 25 bar, temperature at the bottom from 60 to 70° C., from 100 to 150 theoretical plates. The heat consumption of the $C_3$ splitter is preferably covered at least partly by the heat withdrawn from the reaction zone.

The olefin-depleted fraction is discharged from the system. It can, for example, be burnt. It can also be used as feedstock for chemical reactions, e.g. in a steam cracker.

The stream S) taken from the liquid phase for removal of heat in the process of the present invention comprises all feedstocks for the hydroformylation reaction and the catalyst and is, at least until it is brought into contact with the heat exchanger, at the reaction temperature. Thus, the hydroformylation reaction continues in the stream at least until the reaction rate is significantly reduced by withdrawal of heat or until the stream is depleted in one component due to progress of the reaction to such an extent that the hydroformylation stops. This depletion is generally depletion of the gaseous components dissolved in the stream and especially of the carbon monoxide which is generally present in the lowest concentration, based on the starting materials. When the stream is depleted in carbon monoxide, hydrogenation of the olefin by hydrogen still present can then occur as an undesirable secondary reaction. This formation of saturated hydrocarbons results in an undesirable loss of expensive starting materials. To avoid this disadvantage and to make good use as reactor space of the tube volume available up to the point at which the stream is brought into contact with the heat exchanger or even beyond, the reaction component in which the stream is most likely to be depleted is fed into the stream. An advantageous embodiment thus comprises a process as described above in which the reaction proceeds in the stream S) at least until removal of the heat and carbon monoxide and/or hydrogen is fed into this stream before it is depleted in this/these component(s) to such an extent that the remaining components undergo undesirable secondary reactions and/or the hydroformylation effectively stops. The introduction of components into the stream discharged from the reaction zone for removal of heat is carried out by customary methods known to those skilled in the art, e.g. by simple combination of the streams at one or more feed points or via gas distributors, frits, perforated plates, etc.

Particular preference is given to a process in which carbon monoxide is fed into the stream before it is depleted in it to such an extent that the olefin present reacts with the hydrogen still present to form hydrogenation products. This is particularly advantageous when using propene as olefin, since the propene/propane separation is, as described above, extremely costly in terms of apparatus. The formation of propane in the cooling circuit can advantageously be suppressed either completely or to a substantial extent when the procedure described is employed.

The invention is illustrated by the following nonlimiting examples.

EXAMPLES

Comparative Example 1

(Hydroformylation of Propene)

The hydroformylation is carried out using a reactor which is connected to a degassing column and a $C_3$ splitter to separate off and discharge propane. The contents of the reactor are cooled via a discharge stream in an external cooling circuit by means of which the heat of reaction generated in the hydroformylation is removed. 10 t/h of chemical-grade propylene (propane content=5%) and about 6.5 t/h of oxo gas (Co content in the gas phase of the hydroformylation reactor=4%) are continuously fed into the reactor as starting materials.

The amount of the propane stream discharged is 1 t/h, of which 0.5 t/h is propane introduced together with the propylene feed and a further 0.5 t/h is propane formed by hydrogenation of propene. The steam consumption of the degassing column is 1.8 t/h, and that of the $C_3$ splitter is 3.4 t/h.

Example 2

In a reactor system as described in example 1, the heat of reaction generated in the hydroformylation is utilized as energy source for the degassing column and the $C_3$ splitter by passing the heat transfer medium circulating around the external cooling circuit through the corresponding vaporizers of the columns. This results in no steam being required for the splitter and the steam consumption of the degassing column dropping to 0.4 t/h. The total saving of steam is thus 4.8 t/h.

Example 3

The procedure of example 2 is repeated with 220 kg of CO/h being fed into the heat circuit. This reduces the proportion of propane formed by undesired hydrogenation of propene in the external cooling circuit, and the propane stream discharged is reduced to 900 kg/h.

Example 4

The procedure of example 2 is repeated with 250 kg/h of oxo gas being fed into the heat circuit. The propane stream discharged likewise drops to 900 kg/h as a result.

We claim:

1. A hydroformylation process in which at least one olefin having from 2 to 6 carbon atoms is reacted continuously with carbon monoxide and hydrogen in the presence of a hydroformylation catalyst in a reaction zone in which a liquid phase is present and a stream S) is taken from the liquid phase, heat is removed from this stream and the stream is subsequently returned to the reaction zone without removal of a material component, wherein the reaction proceeds in the stream S) at least until the removal of the heat and carbon monoxide and/or hydrogen are/is fed into the stream before it is depleted in these/this component(s) to such an extent that the remaining components undergo undesirable secondary reactions and/or the hydroformylation essentially stops.

2. A process as claimed in claim 1, wherein the heat is withdrawn from the stream S) by bringing it into contact with a heat exchanger.

3. A process as claimed in claim 1, wherein the heat withdrawn from the stream S) is used in a heat-consuming step of the hydroformylation process or of another process.

4. A process as claimed in claim 1, wherein the heat is withdrawn from the stream S) without use of an auxiliary medium for heat transfer.

5. A process as claimed in claim 1, wherein
   i) an olefin-containing feed stream comprising at least one olefin having from 2 to 6 carbon atoms and also carbon monoxide and hydrogen are fed into a reaction zone and reacted in the presence of a hydroformylation catalyst, where a liquid phase is present in the reaction zone and a stream S) is taken from this liquid phase, heat is withdrawn from the stream and the stream is subsequently returned to the reaction zone, without removal of a material component, ii) an output is taken from the reaction zone and is subjected to a single-stage or multistage separation operation to give at least one stream comprising the major part of the hydroformylation product and a stream comprising the major part of the unreacted olefin, and iii) at least part of the stream comprising the major part of the unreacted olefin is returned to the reaction zone.

6. A process as claimed in claim 5, wherein the stream comprising the major part of the unreacted olefin is obtained by firstly separating off a crude hydroformylation product from the output from the reaction zone and subjecting it to a degassing step, with the heat withdrawn from the stream S) being used to cover at least part of the heat requirement of the degassing step.

7. A process as claimed in claim 5, wherein the stream comprising the major part of the unreacted olefin further comprises saturated hydrocarbons and is separated by distillation into an olefin-enriched fraction and an olefin-depleted fraction, with the heat withdrawn from the stream S) being used to cover at least part of the heat requirement of the distillation.

8. A process as claimed in claim 1, wherein carbon monoxide is fed into the stream S) before it is depleted in this to such an extent that the olefin reacts with the hydrogen to form hydrogenation products.

9. A process as claimed in claim 5, wherein carbon monoxide is fed into the stream S) before it is depleted in this to such an extent that the olefin reacts with the hydrogen to form hydrogenation products.

* * * * *